United States Patent [19]

Meilland

[11] Patent Number: Plant 7,667

[45] Date of Patent: Oct. 8, 1991

[54] ROSE PLANT—MEIBEAUSAI VARIETY

[75] Inventor: Alain A. Meilland, Antibes, France

[73] Assignee: The Conard-Pyle Company, West Grove, Pa.

[21] Appl. No.: 526,897

[22] Filed: May 22, 1990

[51] Int. Cl.[5] ..... A01H 5/00

[52] U.S. Cl. ..... Plt./22

[58] Field of Search ..... Plt./22, 23, 24, 26, Plt./27, 11, 1

*Primary Examiner*—Howard J. Locker

*Attorney, Agent, or Firm*—Burns, Doane, Swecker & Mathis

[57] ABSTRACT

A new and distinct variety of Floribunda rose plant is provided which abundantly and continuously forms attractive long lasting large double blossoms. The blossoms are chrome yellow suffused and edged with neyron rose. The plant is semi-erect, compact, bushy, and well-balanced, and exhibits very vigorous vegetation. The new variety is particularly well suited for the decoration of parks and gardens. Good resistance to cryptogamic diseases also is exhibited.

1 Drawing Sheet

SUMMARY OF THE INVENTION

The new variety of Floribunda rose plant was created by artificial pollination wherein two parents were crossed which previously had been studied in the hope that they would contribute the desired characteristics. The female parent (i.e., the seed parent) of the new variety was the Meigurami variety (nonpatented in the United States). The male parent (i.e., the pollen parent) of the new variety was the Meirisouru variety (nonpatented in the United States). The parentage of the new variety can be summarized as follows:

Meigurami × Meirisouru.

The seeds resulting from the above pollination were sown and 70 small plants were obtained which were physically and biologically different from each other. Selective study resulted in the identification of a single plant of the new variety.

The new variety meets well the needs of the horticultural industry for all uses, and is particularly well suited for growing in parks and gardens. Well balanced semi-erect plants are formed which form very elegant buds.

It was found that the new variety of Floribunda rose plant of the present invention possesses the following combination of characteristics:

(a) forms abundantly and continuously attractive long lasting double blossoms which are chrome yellow suffused and edged with neyron rose,
(b) forms very vigorous vegetation,
(c) exhibits a semi-erect, compact, bushy, and well-balanced growth habit, and
(d) is particularly well suited for the decoration of parks and gardens.

The new variety undergoes asexual propagation by various routes, including budding, grafting, cuttage, etc. Asexual reproduction by the above mentioned methods as performed in France shows that the characteristics of the new variety are strictly transmissable from one generation to another.

The new variety has been named the Meibeausai variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and observed during September while budded on *Rosa froebelli* understock and growing outdoors at LeCannet des Maures, Var, France.

FIG. 6 illustrates a specimen of a blooming flower—plan view—obverse;

FIG. 7 illustrates a specimen of a blooming flower—plan view—reverse;

FIG. 8 illustrates a specimen of a fully open flower immediately prior to petal drop—plan view—obverse;

DETAILED DESCRIPTION

Figures 1, 2, 3, 4, 5, 9, 10, 11, 12, 13, 14, 15, 16:
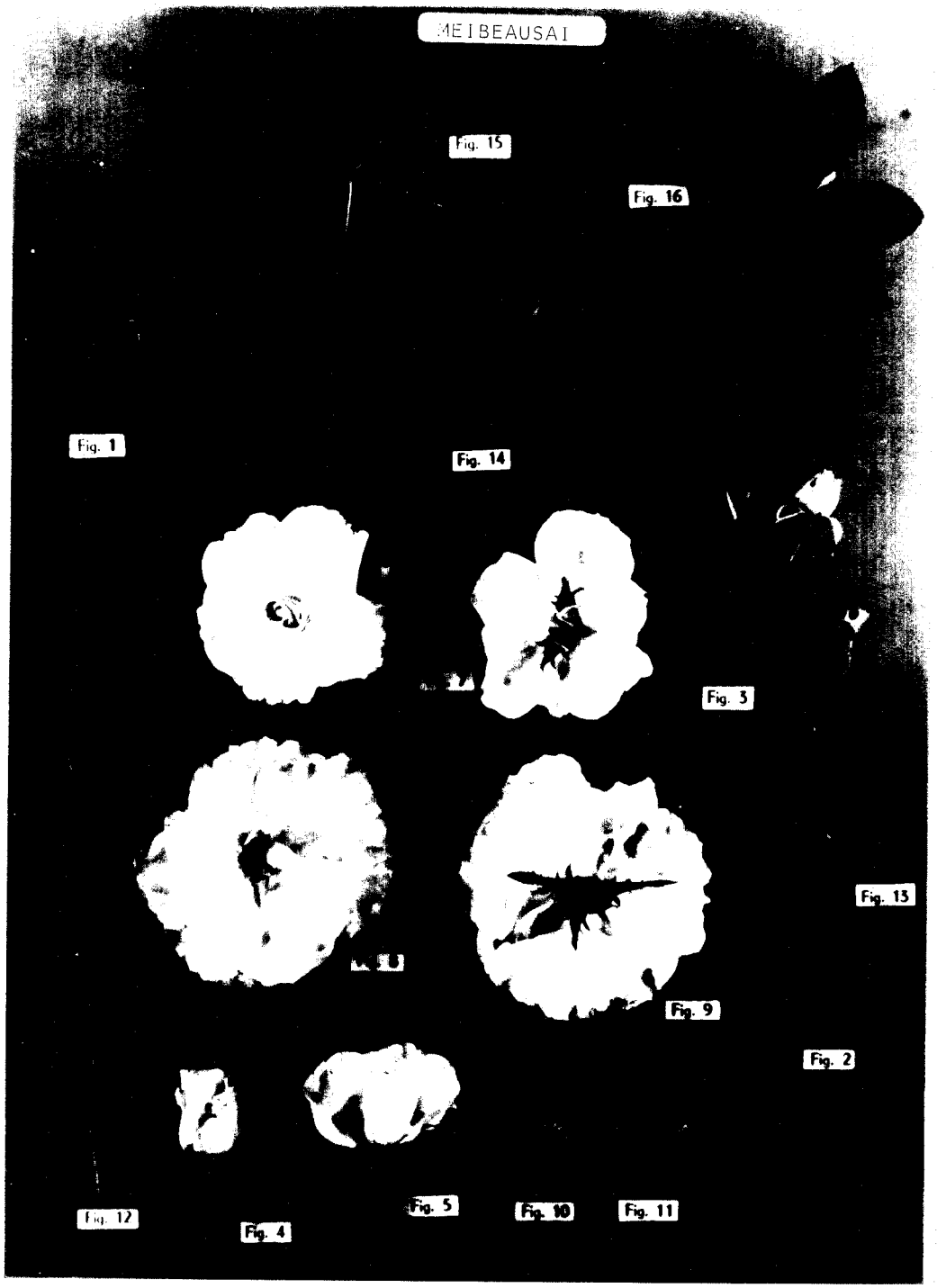
FIG. 1 illustrates a specimen of a young shoot.
FIG. 2 illustrates specimens of two buds before the opening of the sepals.
FIG. 3 illustrates specimens of two buds at the opening of the sepals.
FIG. 4 illustrates a specimen of a floral bud at the opening of the petals.
FIG. 5 illustrates a specimen of a flower in the course of opening.
FIG. 9 illustrates a specimen of a fully open flowers immediately prior to petal drop—plan view—reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a young flowering stem.
FIG. 13 illustrates a specimen of an adult main branch.
FIG. 14 illustrates a specimen of a leaf with three leaflets—plan view—upper surface.
FIG. 15 illustrates a specimen of a leaf with five leaflets—plan view—under surface.
FIG. 16 illustrates a specimen of a leaf with seven leaflets—plan view—upper surface.

The chart used in the identification of the colors is that of The Royal Horticultural Society (R.H.S. Colour Chart). The terminology which precedes reference to the chart has been added to indicate the corresponding colors in more common terms. The description is based on two year old specimens of the new variety during September while grafted on *Rosa froebelli* understock and growing outdoors at LeCannet des Maures, Var, France.

Class: Floribunda.

Plant:

*Height.*—Approximately 70 to 80 cm. on average.

*Habit.*—Semi-erect.

Branches:

*Color.*—Young stems: light green, Green Group 143C, more or less stained with reddish coloration. Adult wood: medium green, Green Group 143B.

*Thorns.*—Size: medium to large. Quantity: moderate. Color: reddish with a greenish tip on young stems and greenish changing to tan on adult wood.

Leaves:

*Stipules.*—Adnate, pectinate, wide and linear.

*Petioles.*—Upper surface: striped reddish brown on young foliage and medium green on adult foliage with glandular edges. Under surface: light green, it bears a few prickles mixed with glandular acicules.

*Leaflets.*—Number: 3, 5, and sometimes 7. Shape: spear-like. Serration: single and regular. Texture: leathery. General appearance: foliage is dense and semi-mat. Color (young foliage): Upper surface: light reddish brown. Under surface: light reddish brown. Color (adult foliage): Upper surface: medium green, Yellow-Green Group 147B. Under surface: light green, Yellow-Green Group 147C.

Inflorescence:

*Number of flowers.*—Approximately 1 to 7 per stem.

*Peduncle.*—Straight, rigid, light green, more or less suffused with reddish coloration, bears numerous pediculate glands, approximately 6 cm. in length on average.

*Sepals.*—Upper surface: tomentose, and greenish, more or less stained with reddish coloration. Under surface: light green, in coloration, more or less stained with reddish coloration, the outside sepals have glandular edges that are only slightly appendiculated.

*Buds.*—Shape: oval. Length: approximately 2.5 cm on average. Size: small. Color upon opening: Upper surface: light mimosa yellow, Yellow Group 8D, slightly edged and suffused with Venetian pink, Red Group 49B. Under surface: light mimosa yellow, Yellow Group 8D.

*Flower.*—Shape: as a flat cup and double. Diameter: approximately 9 to 10 cm. on average. Color (when opening begins): Upper surface: light mimosa yellow, Yellow Group 8D, slightly edged and suffused with Venetian pink, Red Group 49B. Under surface: light chrome yellow, Yellow-White Group 158C. Color (when blooming): Upper surface: light chrome yellow, Yellow-White Group 158D, widely suffused with neyron rose, Red Group 55B. Under surface: pale chrome yellow, Yellow-White Group 158D. Color (at end of opening): Upper surface: light chrome yellow, Yellow-White Group 158D, very widely suffused and edged with neyron rose, Red Group 55B. Under surface: pale chrome yellow, Yellow-White Group 158D. Fragrance: none. Lasting quality: long. Petal drop: good. Petal number: approximately 24 to 25 on average. Petal texture: consistent. Petal form: oval with a corrugated tip. Stamen number: approximately 88 to 94 on average. Anthers: ochre, normal. Filaments: free standing, greenish straw, of irregular heights. Pistils: approximately 47 to 52 on average. Stigmas: normal, yellowish in coloration, located at substantially the same level as the anthers. Styles: tomentose at base, straw colored turning fuschia at the top, more or less twisted, of irregular heights. Receptacle: medium green, smooth, and in longitudinal section it is narrow and in the shape of a funnel.

Development:

*Vegetation.*—Vigorous.

*Blooming.*—Very floriferous with continuous blooming throughout the season.

*Apptitude to bear fruit.*—Good.

*Resistance to disease.*—Good.

*Resistance to frost.*—Very good.

I claim:

1. A new and distinct variety of Floribunda rose plant characterized by the following combination of characteristics:

(a) forms abundantly and continuously attractive long lasting double blossoms which are chrome yellow suffused and edged with nyron rose, (b) forms very vigorous vegetation, (c) exhibits a semi-erect, compact, bushy and well-balanced growth habit, and (d) is particularly well suited for the decoration of parks and gardens;

substantially as herein shown and described.

* * * * *

MEIBEAUSAI